United States Patent [19]

Fodor et al.

[11] Patent Number: 4,923,888

[45] Date of Patent: May 8, 1990

[54] BUTENOIC ACID AMIDES, THEIR SALTS, AND PHARMACEUTICAL COMPOSITIONS CONTAINING THEM

[75] Inventors: Tamás Fodor; Láaszló Dobay; Jáanos Fischer; Béla Stefkóo; Eleméer Ezer; Judit Matuz; Katalin Sághy; Láaszló Szporny, all of Budapest, Hungary

[73] Assignee: Richter Gedeon Vegyeszeti Gyar RT, Budapest, Hungary

[21] Appl. No.: 248,969

[22] Filed: Sep. 26, 1988

[30] Foreign Application Priority Data

Sep. 25, 1987 [HU] Hungary ............................... 4302/87

[51] Int. Cl.$^5$ .......................................... A61K 31/40
[52] U.S. Cl. .................... 514/414; 514/417;
514/533; 514/541; 548/462; 548/477; 560/36;
560/39; 560/41; 562/441; 562/444; 562/448;
562/449; 562/450
[58] Field of Search ............... 560/39, 41, 36;
562/441, 444, 448, 449, 450, 441; 548/477, 462;
514/533, 541, 563, 417, 414

[56] References Cited

FOREIGN PATENT DOCUMENTS 0099960 2/1984 European Pat. Off. ............. 560/41
0239062 9/1987 European Pat. Off. ............. 560/41

*Primary Examiner*—Bruce D. Gray

*Attorney, Agent, or Firm*—Herbert Dubno; Jonathan Myers

[57] ABSTRACT

The present invention relates to novel compounds of the general formula (I),

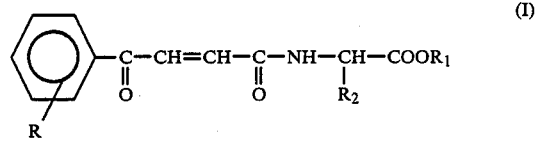

wherein
R stands for hydrogen, halogen, $C_{1-4}$ alkyl, $C_{1-4}$ alkoxy or $C_{1-4}$ acylamino group;
$R_1$ means hydrogen or a carboxyl-protective group; and
$R_2$ represents a —$(CH_2)_n$—$CO_2R_5$ group, wherein n is 1, 2, 3 or 4; and
$R_5$ stands for hydrogen or a carboxyl-protective group; or
$R_2$ means a —$(CH_2)_n$—$NH_2$ group, wherein n is 1, 2, 3 or 4 of E and/or Z configurtion as well as their salts.

The compounds according to the invention show a cytoprotective effect and promote the healing of the stomach ulcer. Their toxicity is low.

4 Claims, No Drawings

BUTENOIC ACID AMIDES, THEIR SALTS, AND PHARMACEUTICAL COMPOSITIONS CONTAINING THEM

FIELD OF THE INVENTION

This invention relates to novel 4-oxo-4-(substituted phenyl)butenoic acid amides of E and/or Z configuration as well as their salts having a cytoprotective action.

BACKGROUND OF THE INVENTION

Several compounds close to these compounds concerning both their type of activity and chemical structure, have been described in the British patent specification No. 2,096,999. One of the most effective compounds claimed in this cited patent specification was found to be 4-oxo-4-(3,4,5-trimethoxyphenyl)butenoic acid prepared by dehydrating the product obtained from the aldol condensation of 3,4,5-trimethoxyacetophenone with glyoxylic acid. The yield of the aldol reaction amounted to 28%, that of the dehydration to 71%, which means a total yield of only 20%.

OBJECT OF THE INVENTION

The object of the present invention is to provide novel, therapeutically useful compounds which can be prepared in a good yield from simple, commercially available starting substances.

DESCRIPTION OF THE INVENTION

The present invention relates to novel compounds of the formula (I),

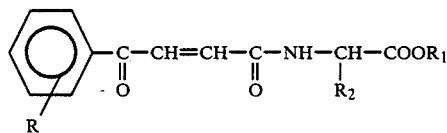

wherein
R = stands for hydrogen, halogen, $C_{1-4}$alkyl, $C_{1-4}$alkoxy of $C_{1-4}$acylamino group;
$R_1$ = means hydrogen or a carboxyl-protective group; and
$R_2$ = represents a $-(CH_2)_n-CO_2R_5$ group, wherein n is 1, 2, 3 or 4; and
$R_5$ stands for hydrogen or a carboxyl-protective group; or
$R_2$ = means a $-(CH_2)_n-NH_2$ group, wherein n is 1, 2, 3 or 4
of E and/or Z configuration as well as their salts and pharmaceutical compositions containing these compounds.

The compounds of the formula (I) contain a double bond and thus can exist in the form of the E or Z geometrical isomer.

According to an other aspect of the invention, there is provided a process for the preparation of new compounds of the formula (I), wherein
R = stands for hydrogen, halogen, $C_{1-4}$alkyl, $C_{1-4}$alkoxy or $C_{1-4}$acylamino group;
$R_1$ = means hydrogen or a carboxyl-protective group; and
$R_2$ = represents a $-(CH_2)_n-CO_2R_5$ group, wherein n is 1, 2, 3 or 4; and
$R_5$ stands for hydrogen or a carboxyl-protective group; or
$R_2$ = means a $-(CH_2)_n-NH_2$ group, wherein n is 1, 2, 3 or 4
of E and/or Z configuration as well as their salts, which comprises reacting a compound of the formula (II),

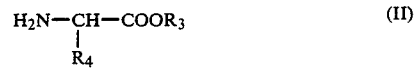

wherein
$R_3$ = is a carboxyl-protective group; and
$R_4$ = means a $-(CH_2)_n-CO_2R_6$ group, wherein n is 1, 2, 3 or 4 and
$R_6$ stands for a carboxyl-protective group; or
$R_4$ = represents a $-(CH_2)_n-NHR_7$ group, wherein n is 1, 2, 3 or 4 and
$R_7$ stands for an amino-protective group,
or an acid addition salt thereof with a substituted butenoic acid of the formula (III),

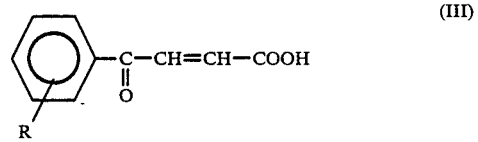

wherein R is as defined above, or with a carboxyl group-activated derivative thereof, and if desired, removing any optionally present protective group in a known manner and/or, if desired, changing in the obtained compound of the general formula (I) the configuration, determined by the double bond, in a known way.

If desired, the compounds of the formula (I) containing a free carboxyl group can be converted to pharmaceutically acceptable salts with inorganic or organic bases; or, when $R_2$ in the formula (I) stands for a $-(CH_2)_n-NH_2$ group, a pharmaceutically valuable acid addition salt thereof may also be prepared.

The compounds of the formula (I) are effective cytoprotective substances.

The starting materials are commercially available or can be prepared by methods described in the literature. Thus, the preparation of 4-oxo-4-phenyl-2(E)-butenoic acid has been described in Org, Synth, Coll. Vol. 3, page 109 (1955); 4-(4-methylphenyl)-4-oxo-2(E)-butenoic acid has been prepared according to Pechman [(Berichte 15, 888 (1982)] whereas 4-(4-methoxyphenyl)-4-oxo-2(E)-butenoic acid has been synthesized according to Papa et al. [J. Am. Chem. Soc. 70, 3356 (1948)]. The amino esters of the formula (II) were prepared as described in: Houben-Weyl: "Methoden der organischen Chemie", Vol. 15/1, pp. 316 –340, G. Thieme Verlag, Stuttgart (1974).

It has been found in the course of our investigations that the reaction of the starting substances could be carried out with a yield of 40 to 70% under the usual conditions.

In the process of the present invention, a substituted butenoic acid of the formula (II), or a carboxylic group-activated derivative thereof, which may have E or Z configuration based on the geometry of the double bond, is reacted with an amino acid derivative of the formula (II) in an inert organic solvent. Activated derivatives of the compounds of formula (III) are their esters, acid halides or acid anhydrides or a derivative formed with an activating (coupling) reagent, each of which can be prepared in a manner known per se. Carbodiimides such as N,N-dicyclohexylcarbodiimide may preferably be used as activating reagents.

Other activating reagents have been described in a monography by M. Bodánszky: "Principles of Peptide Synthesis", Springer Verlag, Berlin, Heidelberg, New York and Tokyo (1984). The compounds of the formula (II) have to be reacted in a carboxyl group protected form. Straight or branched chain $C_{1-4}$alkyl groups, preferably a tert.-butyl, diphenylmethyl, trimethylbenzyl or phthalimidomethyl group [R. W. Roeske: "The Pepides", Vol. 3., page 101 (1981) as well as T. W. Green "Protective Groups in Organic Synthesis", Ed.. John Wiley, New York, Chichester, Brisbane, Toronto and Singapore (1981)] may preferably be used for protection. When it is desired to prepare compounds of the formula (I), wherein $R_2$ is a —$(CH_2)_n$—$NH_2$ group, then the amino group of the corresponding compound of formula (II) also has to be protected. All protective groups used in the peptide chemistry, such as the tert.-butoxycarbonyl group [R. Schwyzer and W. Rittel: Helv. Chim. Acta 44, 159 (1961)] are useful for this purpose. These reactions are carried out in an inert organic solvent, preferably dichloromethane at a temperature between $-10°$ C. and $+20°$ C.

If desired, the E and Z isomers of the compounds of formula (I) can be converted into each other: e.g. a compound of E configuration can be converted to the product of Z configuration under the effect of e.g. UV light in the presence of an inert organic solvent.

The compounds of the formula (I) containing hydrogen as $R_1$ or $R_5$, respectively are prepared by removing the group different from hydrogen (suitably the tert.-butyl group), which is bound to the carboxyl group in question, in a known way e.g. by using trifluoroacetic acid.

In the course of our pharmacological study it has been found that, when used even in a lower dose, the compounds of the formula (I) show a cytoprotective action (with an oral $ED_{50}$ value of 2 to 5 mg/kg). This could be demonstrated by using the method of A. Robert [Gastroenterology 77, 761–767 (1979)] as follows.

Starved rats were given absolute ethanol containing concentrated hydrochloric acid which induced longitudinal bleedings in the glandular part of the stomach within a short time. This damaging effect is prevented by cytoprotective substances.

The oral $ED_{50}$ values of some compounds according to the invention, which were examined in the acid-ethanol test, are shown in Table 1.

The compounds investigated were as follows:
A: diethyl N-[4-oxo-4-phenyl-2(E)-butenoyl]-(S)-aspartate;
B: diethyl N-[4-oxo-4-phenyl-2(E)-butenoyl]-(RS)-aspartate; and
C: diethyl N-[4-oxo-4-phenyl-2(E)-butenoyl]-(R)-aspartate.

TABLE 1

Oral $ED_{50}$ values of some compounds according to the invention in the acid-ethanol test

| Compound studied | Cytoprotective effect $ED_{50}$ (mg/kg p.o.) |
|---|---|
| A (S) | 3.8 |
| B (RS) | 2.6 |

TABLE 1-continued

Oral $ED_{50}$ values of some compounds according to the invention in the acid-ethanol test

| Compound studied | Cytoprotective effect $ED_{50}$ (mg/kg p.o.) |
|---|---|
| C (R) | 1.7 |

The compound C is not toxic in an oral dose of 1200 mg/kg.

The investigation of (the effect promoting the healing of) the chronic stomach ulcer induced by acetic acid was carried out as follows.

In the course of examining the healing-promoting effect, one of the most widely used methods namely, the so-called acetic acid-induced chronic stomach ulcer model was used [Takagi et. al.: Jap. J. Pharmacol. 19, 418–426 (1969)]

The abdominal wall of anaesthetized rats was opened and 50 μl of a 20% acetic acid solution were injected into the stomach wall, then the abdominal wall of the animal was sutured. The treatment by the test compounds was started on day 5 following the surgical operation and continued until day 14 by using the daily doses shown in Table 2. Then, the animals were killed and their stomachs were examined. The extent of ulceration was assessed by measuring the diameter of the ulcer, wherefrom the size of the damaged area could be calculated. For characterizing the degree of the cicatrization, the change in the ulcer index measured in the treated animals was related to the values measured in the untreated (control) animals and expressed as percentage values. The results of these investigations are summarized in Table 2.

TABLE 2

Stereospecific effect of some compounds on promoting the healing of the chronic stomach ulcer in rats

| Treatment by compound No. | No. of animals | Dose mg/kg/day p.o. | Ulcer index mm²/stomach | Change in the ulcer index related to the control |
|---|---|---|---|---|
| Control | 98 | — | 11.5 ± 1.0 | — |
| B (RS) | 7 | 30 × 10 | 4.2 ± 1.8$^{xx}$ | 63% ↑ |
|  | 9 | 10 × 10 | 7.7 ± 2.8 | 34% ↑ |
| A (S) | 17 | 40 × 10 | 13.4 ± 2.1 | 11% ↓ |
| C (R) | 9 | 10 × 10 | 2.7 ± 1.1$^{xx}$ | 77% ↑ |
|  | 10 | 3 × 10 | 5.0 ± 1.2$^{xx}$ | 57% ↑ |
|  | 9 | 1 × 10 | 13.1 ± 3.5 | 13% ↓ |

↑ : Promotion of the healing
↓ : Delaying of the healing
± S.E.M; $^{xx}$P <0.01 as compared to the control by using Student's "t" test.

TABLE 3

Effect of some reference drugs on promoting the healing of the chronic stomach ulcer induced by acetic acid

| Name of the drug | Dose mg/kg/day p.o. | Change in the ulcer index related to the control |
|---|---|---|
| Cimetidine | 50 × 10 | 17% ↑ |
| Pirenzepine | 12 × 10 | 13% ↑ |
| Sucralfate | 500 × 10 | 55% ↑ |
| Cetraxate | 150 × 10 | 49% ↑ |
| MMSC$^x$ | 50 × 10 | 59% ↑ |
| Spizofuron | 50 × 10 | 11% ↑ |

$^x$Methylmethionine sulfonium chloride
↑ : Promotion of the healing
↓ : Aggravation of the ulcer It can be seen from Table 1 that the R isomer of diethyl N-[4-oxo-4-phenyl-2(E)-butenoyl]-aspartate is the most effective in the cytoprotective test.

It is obvious from Table 2 that the healing of the ulcer was significantly (by 57%) accelerated by even a 3 mg/kg oral dose of the R isomer whereas the healing was not promoted by even a 40 mg/kg oral dose of the S isomer. It can be stated that a highly significant difference exists between the healing-promoting effects of the R and RS modifications.

From Table 3 it appears that the healing-promoting effect of the R isomer greatly exceeds that of the reference drugs which are at present being used in the human therapy or are under clinical trial.

The toxicity values of the substances according to the invention are very favorable since no toxic symptoms were observed after the single oral administration of even 1500 mg/kg.

The invention is illustrated in detail by the following non-limiting Examples.

EXAMPLE 1

Preparation of diethyl N-[4-oxo-4-phenyl-2(E)-butenoyl]-(S)-aspartate 10.3 g (0.05 mol) of dicyclohexylcarbodiimide dissolved in 20 ml of anhydrous dichloromethane are dropped to the solution containing 8.8 g (0.05 mol) of 4-oxo-4-phenyl-2(E)-butenoic acid in 80 ml of anhydrous dichloromethane at a temperature between $-5°$ C. and $-10°$ C. After stirring for 15 minutes, 11.3 g (0.05 mol) of diethyl (S)-aspartate hydrochloride dissolved in 30 ml of anhydrous dichloromethane, then 5.05 g (0.05 mol) of N-methylmorpholine dissolved in 20 ml of anhydrous dichloromethane are added dropwise to the reaction mixture. After stopping of the cooling, the mixture is stirred for 4 hours, the solid precipitate is filtered and washed with dichloromethane. The filtrate is successively extracted twice with 50 ml of 5% sodium hydrogen carbonate solution each, 50 ml of water, twice with 50 ml of 1 N hydrochloric acid each and finally with 50 ml of water, then dried over anhydrous magnesium sulfate and evaporated. After recrystallizing the residue from ether, a yield of 8.5 g (49%) of the title compound is obtained, m.p.: 91°–93° C.

(After recrystallizing this substance from a 2.5:1 mixture of cyclohexane and benzene 5.8 g of product are obtained, m.p.: 91°–92° C., $[\alpha]^{25}$ $-20.7°$ (c=2, ethanol).

Analysis: Calculated for $C_{18}H_{21}NO_6$: C 62.24; H 6.09; N 4.03%; found: C 62.22; H 6.34; N 3.98%.

EXAMPLE 2

Preparation of diethyl N-[4-oxo-4-phenyl-2-(E)-butenoyl]-(R,S)-aspartate

The process described in Example 1 is followed, expect that 11.3 g (0.05 mol) of diethyl (R,S)-aspartate are used as starting substance to given 7.11 g (41%) of the named compound, m.p.: 84°–86° C.

Analysis: Calculated for $C_{18}H_{21}NO_6$: C 62.24; H 6.09; N 4.03%; found: C 62.25; H 6.40; N 4.01%.

EXAMPLE 3

Preparation of diethyl N-[4-oxo-4-phenyl-2(E)-butenoyl]-(S)-glutamate

The process described in Example 1 is followed, except that 11.97 g (0.05 mol) of diethyl (S)-glutamate are used as starting substance to give 7.05 g (39%) of the named compound, m.p.: 83°–85° C., $[\alpha]_D^{25}$ $-30.95°$ (c=2, ethanol).

Analysis: Calculated for $C_{19}H_{23}NO_6$: C 63.15; H 6.41; N 3.87%; found: C 63.04; H 6.43; N 3.76%.

EXAMPLE 4

Preparation of ethyl Nα-[4-0x0-4-phenyl-2(E)-butenoyl]-(S)-lysinate hydrochloride Step (a)

Preparation of ethyl Nα-[4-oxo-4-phenyl-2(E)-butenoyl]-Nϵ-(tert.-butoxycarbonyl)-(S)-lysinate A solution containing 10.3 g (0.05 mol) of dicyclohexylcarbodiimide in 20 ml of anhydrous dichloromethane is added dropwise to the solution of 8.8 g (0.05 mol) of 4-oxo-4-phenyl-2(E)-butenoic acid in 80 ml of anhydrous dichoromethane at $-10°$ C. After stirring for 15 minutes, 15 g (0.05 mol) of ethyl Nϵ-(tert.-butoxycarbonyl)-(S)-lysinate hydrochloride dissolved in 120 ml of anhydrous dichloromethane, then 5.05 g (0.05 mol) of N-methylmorpholine dissolved in 10 ml of anhydrous dichloromethane are added dropwise to the reaction mixture. After stirring for 4 hours, the precipitated dicyclohexylurea is filtered and washed with dichloromethane. The filtrate is successively extracted twice with 50 ml of 5% sodium hydrogen carbonate solution each, with water, twice with 50 ml of 1 N hydrochloric acid each, finally with 50 ml of water and dried over anhydrous magnesium sulfate. After evaporating the solvent under reduced pressure, the oily residue is crystallized from a mixture of benzene and petroleum ether (b.p. 70° C.) to give 15.8 g (73%) of the named product of Step a), m.p.: 91°–94° C.

Step (b)

Preparation of ethyl Nα-[4-oxo-4-phenyl-2(E)-butenoyl]-(S)-lysinate hydrochloride 12 g (0.027 mol) of the product obtained in Step (a) are stirred for 2 hours with 80 ml of trifluoroacetic acid cooled to 0° C., then the trifluoroacetic acid is evaporated under reduced pressure. The residue is dissolved in 30 ml of acetonitrile and crystallized by adding 100 ml of diethyl ether to give 9.98 g (83%) of the trifluoroacetate salt, m.p.: 119°–121° C.

4.46 g (0.01 mol) of this trifluoroacetate salt are dissolved in 40 ml of acetonitrile, 2.6 ml of a 6 N dioxanic hydrogen chloride solution are added and crystallized by adding 100 ml of diethyl ether under cooling to give 2.95 g (80%) of the named compound of Step b), m.p.: 114°–118° C., $[\alpha]_D^{25}$ $-31.84°$(c=2, ethanol).

Analysis: Calculated for $C_{18}H_{24}N_2O_4 \cdot HCl$: C58.62; H 6.83; N 7.59; Cl 9.61%; found: C 58.57; H 6.94; N 7.54; Cl 9.65%.

EXAMPLE 5

Preparation of N-[4-oxo-4-phenyl-2(E)-butenoyl]-(S)-aspartic acid

A suspension containing 6.71 g (0.02 mol) of di(tert.-butyl) (S)-aspartate oxalate in 25 ml of dichloromethane is extracted with a solution containing 4.14 g of potassium carbonate in 20 ml of water. The aqueous phase is extracted thrice with 20 ml of dichloromethane each, dried over anhydrous magnesium sulfate and evaporated to a volume of 50 ml. After adding 3.52 g (0.02 mol) of 4-oxo-4-phenyl-2(E)-butenoic acid, the solution is cooled to 0° C. and 4.12 g (0.02 mol) of dicyclohexylcarbodiimide dissolved in 10 ml of abs. dichloromethane are added dropwise to the reaction mixture at the same temperature. After stirring the mixture at 0° C. for 1 hour and then at room temperature for 1 hour, the dicyclohexylurea is filtered and washed with dichloromethane. The filtrate is successively extracted twice with 20 ml of 0.1 N hydrochloric acid each, 50 ml of water, twice with 20 ml of 5% sodium hydrogen carbonate solution each and finally with 50 ml of water. After drying over anhydrous magnesium sulfate and evaporating the solvent, the oily residue is dissolved in 40 ml of an 1:1 mixture of dichloromethane and trifluoroacetic acid and let to stand at room temperature for 20 hours. After evaporating the solvent, the residue is crystallized for diethyl ether to give 2.34 g (40%) of the title compound, m.p.: 154°–156° C., $[\alpha]_D^{20}$ −7.29° (c=2, mehanol).

PREPARATION OF THE MAGNESIUM SALT OF THE TITLE COMPOUND 2 g (6.8 mmol) of N-[4-oxo-4-phenyl-2(E)-butenoyl]-(S)-aspartic acid are dissolved in the solution of 0.76 g (13.6 mmol) of potassium hydroxide in 5 ml of distilled water and 1.51 g (6.8 mmol) of said magnesium perchlorate are added. The precipitated potassium perchlorate is filtered, the filtrate is evaporated and after adding acetonitrile, the product obtained is filtered to give 1.81 g (85%) of the magnesium salt of the named compound, m.p.: >360° C., $[\alpha]_D^{20}$ +23.9° (c=2, methanol/water=4:1).

EXAMPLE 6

Preparation of diethyl N-[4-oxo-4-phenyl-2(E)-butenoyl]-(R)-aspartate

A solution containing 21.6 g (0.105 mol) of dicyclohexylcarbodiimide in 40 mol of anhydrous dichloromethane is added dropwise to the solution of 17.6 g (0.1 mol) of 4-oxo-4-phenyl-2(E)butenoic acid in 100 ml of anhydrous dichloromethane at 0° C. After stirring for 30 minutes, 22.55 g (0.1 mol) of diethyl (R)-aspartate hydrochloride dissolved in 100 ml of dichloromethane and then 10.1 g (0.1 mol) of N-methylmorpholine dissolved in 20 ml of anhydrous dichloromethane are added. The reaction mixture is stirred under cooling by ice-water for 3 hours and then at room temperature for 15 hours. The precipitated solid dicyclohexylurea (DCU) is filtered and the filtrate is successively extracted with 5% sodium hydrogen carbonate solution, water, 1 N hydrochloric acid and finally with water. After drying over anhydrous magnesium sulfate and filtering the drying agent, the solvent is evaporated and the residue is crystallized from a 10:1 mixture of cyclohexane and benzene. 24.7 g (71%) of the product are obtained. After recrystallization from diisopropyl ether, 19.4 g (56%) of the named compound are obtained, m.p.: 88°–89° C., $[\alpha]_D^{25}$ +12.2 (c=2, ethanol).

We claim:

1. A 4-Oxo-4-(substituted phenyl)butenoic acid amide of the formula (I),

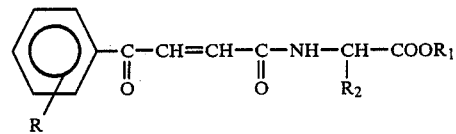

wherein

R = stands for hydrogen, halogen, $C_{1-4}$alkyl, $C_{1-4}$alkoxy or $C_{1-4}$acylamino group;

$R_1$ = means hydrogen or a carboxyl-protective group selected from the group consisting of $C_{1-4}$alkyl, diphenylmethyl, trimethylbenzyl and phthalimidomethyl; and $R_2$ = represents a —$(CH_2)_n$—$CO_2R_5$ group, wherein n = is 1, 2, 3 or 4; and $R_5$ = stands for hydrogen or a carboxyl-protective group selected from the group consisting of $C_{1-4}$alkyl, diphenylmethyl, trimethylbenzyl and phthalimidomethyl; or $R_2$ = means a —$(CH_2)_n$—$NH_2$ group, wherein n is 1, 2, 3 or 4 of E and/or Z configuration or a salt thereof.

2. Diethyl N-[4-oxo-4-phenyl-2(E)-butenoyl]-(R)-aspartate.

3. A pharmaceutical composition which comprises as active ingredient a 4-Oxo-4-(substituted phenyl)-butenoic acid amide of the formula (I),

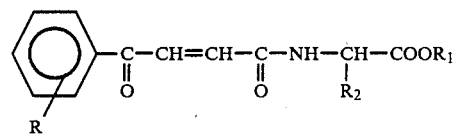

wherein

R = stands for hydrogen, halogen, $C_{1-4}$alkyl, $C_{1-4}$alkoxy or $C_{1-4}$acylamino group;

$R_1$ = means hydrogen or a carboxyl-protective group selected from the group consisting of $C_{1-4}$alkyl, diphenylmethyl, trimethylbenzyl, and phthalimidomethyl; and $R_2$ = represents a —$(CH_2)_n$—$CO_2R_5$ group, wherein n = is 1, 2, 3 or 4; and $R_5$ = stands for hydrogen or a carboxyl-protective group selected from the group consisting of $C_{1-4}$alkyl, diphenylmethyl, trimethylbenzyl and phthalimidomethyl; or $R_2$ = means a —$(CH_2)_n$—$NH_2$ group, wherein n = is 1, 2, 3 or 4 of E and/or Z configuration or a pharmaceutically acceptable salt thereof, in admixture with a pharmaceutical carrier.

4. A method of treating an ulcer in a mammalian subject which comprises the step of administering to the subject an effective amount of a compound as defined in claim 1.

* * * * *